Figure 1:
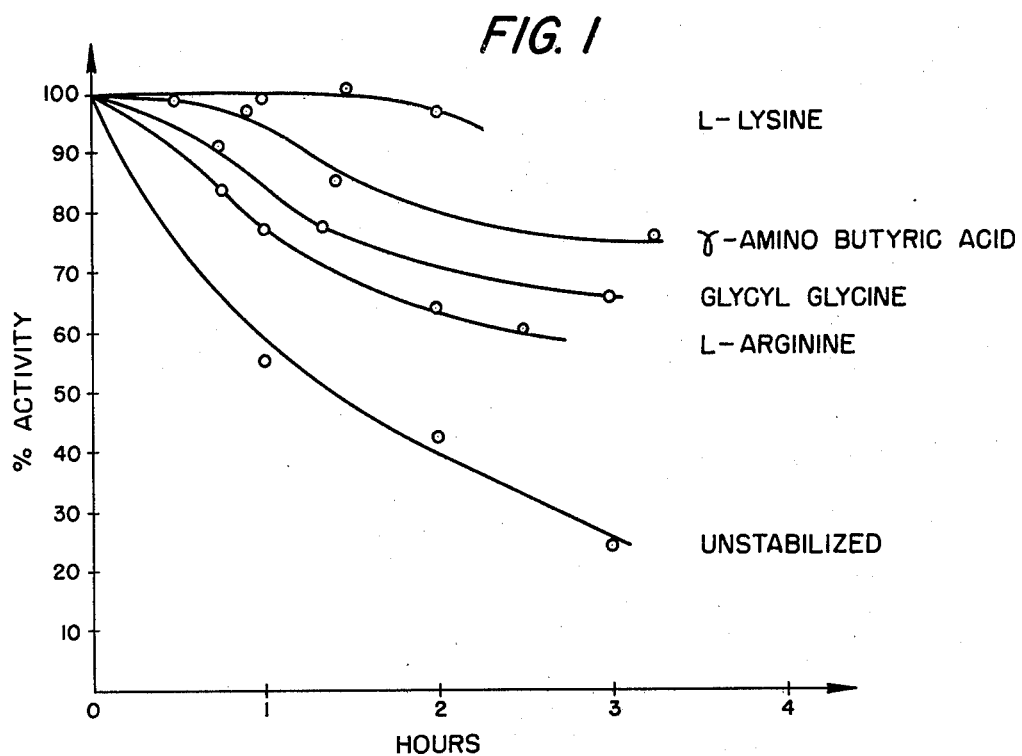

United States Patent [19]

Jensen

[11] 3,950,513

[45] Apr. 13, 1976

[54] PROCESS OF STABILIZING THERAPEUTICALLY USEFUL PLASMIN SOLUTIONS

[75] Inventor: Villy Johannes Jensen, Copenhagen Vanlose, Denmark

[73] Assignee: Novo Terapeutisk Laboratorium A/S, Denmark

[22] Filed: Sept. 19, 1969

[21] Appl. No.: 860,172

Related U.S. Application Data

[63] Continuation of Ser. No. 519,809, Dec. 3, 1969, abandoned, which is a continuation-in-part of Ser. No. 189,367, April 23, 1962, abandoned.

[52] U.S. Cl. .................................. 424/94; 195/63
[51] Int. Cl.² ................... A61K 37/48; G07F 11/00
[58] Field of Search .......... 424/94; 195/63, 66 B, 68

[56] References Cited
UNITED STATES PATENTS

| | | | |
|---|---|---|---|
| 3,051,627 | 8/1962 | Bradford et al. | 424/94 |
| 3,066,079 | 11/1962 | Hagen et al. | 195/66 |
| 3,434,929 | 3/1969 | Buck et al. | 195/66 |

OTHER PUBLICATIONS

Alkjaersig et al, J. Biol. Chem., Vol. 234, No. 4, pp. 832–837, Apr. 1959.

Cliffton, Annals of the New York Academy of Science, Vol. 68, Art. 1, pp. 209–210, Aug. 30, 1957.

Igawa et al, *Keio J. Medicine*, Vol. 8, No. 4, 225–233, Dec. 1959.

Storm et al, *Acta Chir. Scand*, suppl., Vol. 283, pp. 315–321, 1961.

*Primary Examiner*—Richard L. Huff
*Attorney, Agent, or Firm*—Robert E. Burns; Emmanuel J. Lobato; Bruce L. Adams

[57] ABSTRACT

Plasmin compositions containing a concentration of plasmin sufficiently great for therapeutic administration are stabilized by the addition thereto of a physiologically nontoxic amino acid.

18 Claims, 2 Drawing Figures

PROCESS OF STABILIZING THERAPEUTICALLY USEFUL PLASMIN SOLUTIONS

This application is a continuation of application Ser. No. 519,809 filed Dec. 3, 1969, which is a continuation-in-part of application Ser. No. 189,367 filed Apr. 23, 1962 both now abandoned. The present invention relates to therapeutically useful compositions containing plasmin as the essential active ingredient, a process for the preparation of such compositions, and a method for the clinical use of said therapeutically useful plasmin compositions.

One object of the invention is to provide a stable, therapeutically useful composition containing plasmin as the essential active ingredient.

Another object of the invention is to provide a stable, therapeutically useful composition in solid form and containing plasmin as the essential active ingredient.

A further object of the invention is to provide a method for preparing a stable, therapeutically useful plasmin composition ready for clinical use.

A still further object of the invention is to provide a method for the clinical use of stable compositions containing plasmin as the essential active ingredient by way of intravenous administration.

Other objects and advantages of the present invention will be apparent from the following description.

It is known to use sterile plasmin solutions for different therapeutic purposes in which it is endeavoured to utilize the proteolytic properties of the plasmin. The mode of administration depends on the character of the malady which it is intended to relieve or to cure. Thus, use has been made of injections e.g. in case of empyema, hemothorac and sinusitis, and infusions, e.g. in case of thromboses and edemata. Further use has been made of instillations, e.g. in connection with fistulae of different kind and vaginitis. Use has also been made of surface application, e.g. in connection with wound treatments.

Usually the activity of plasmin solutions is expressed in the number of plasmin units per milliliter. However, no definition of a plasmin unit has until now been internationally adopted. Here and in the following one plasmin unit means the amount of plasmin causing in 20 minutes the formation of decomposition products being soluble in perchloric acid and having an extinction of 1 unit at 275 m$\mu$ under the following experimental conditions:

1 milliliter of the plasmin solution the activity of which is to be determined and the pH of which is 7.5 is added to two test tubes each containing in 0.4 molar phosphate buffer (pH 7.50) 1 milliliter of a 3 per cent's solution of Hammarsten Casein said solution having been preheated to 35.5°C. After standing for 2 minutes in thermostat at 35.5°C there are added to one of the tubes 3 milliliters of a 1.7 molar solution of perchloric acid in distilled water, and after standing for 22 minutes at 35.5°C there is added to the other tube the same quantity of perchloric acid solution. By the addition of the perchloric acid a precipitation takes place, and the two test tubes now stand for 20 minutes whereafter filtration two times through filtering paper (J. H. Munktells unrivalled Genuine Swedish Filtering Paper No. 0.9 cm) is carried out. The extinction of the two solutions is thereafter measured at 275 m$\mu$ in a Beckman D U Spectrophotometer (1 cm quartz cuvette), the value of the sample having stood for 2 minutes being used as blind value. The plasmin solution the activity of which is to be determined is diluted to such an extent that the extinction does not exceed 0.5 as at higher plasmin concentrations no proportionality exists between the extinction and the plasmin concentration.

While an aqueous plasmin solution having a pH-value of 2 to 3 is practically completely stable at temperatures up to 35°C, the same plasmin solution with neutral reaction (pH 7 or the pH of the blood) is unstable provided the solution has not been greatly diluted. If one makes it a condition that the highest loss of plasmin permissible in the solution in the course of 2 hours at 25°C is 20 per cent, plasmin solutions containing more than about 0.1 unit per milliliter must be considered unstable.

As the plasmin solutions used for therapeutic purposes contain considerably more plasmin such as 0.4 units per milliliter or more, preferably at least 1 unit per milliliter, one has hitherto been compelled to use freshly prepared plasmin solutions and to put up with possible losses of plasmin.

The present invention aims at making possible the production of clinical useful plasmin solutions being considerably more stable than are the hitherto known plasmin solutions. A further object of the invention is to furnish plasmin solutions being practically stable even at a temperature of about 35°C.

The invention is based on the novel scientific observation that the stability of therapeutically useful plasmin solutions containing plasmin in an amount of at least 0.4 units per milliliter, preferably at least 1 unit per milliliter, can be considerably improved by adding thereto one or more physiologically non-toxic amino acids in an amount of at least 0.002 millimoles per plasmin unit, preferably in an amount of 0.02 to 1 millimole per plasmin unit. Several investigators have previously carried out scientific tests in respect of the effect caused by an addition of different amino acids to aqueous systems containing plasmin and its proenzyme plasminogen. These tests have shown that according to their chemical structure the employed amino acids, even in very low concentrations are able to inhibit the conversion of the plasminogen into plasmin to a more or less pronounced degree and thereby to prevent temporarily a plasmin activity in vivo. This does not, however, permit to draw any conclusions as to the influence of amino acids on the stability and activity of plasmin solutions. On the background of what was known in the present field it must be said to be surprising that amino acids are able to impart to aqueous plasmin solutions a highly increased stability rendering them more suitable for practical clinical use, especially for infusion.

It has been described in literature that partially purified plasmin from human plasma is unstable in neutral solutions, as demonstrated by a rapid loss of proteolytic activity at 37°C, and it has been suggested that this lability is due to self-digestion of plasmin. Furthermore, it has been demonstrated that urea and methylamine may inhibit this autolysis.

In addition, it has also been disclosed in literature that a specific amino acid, namely ϵ-amino caproic acid, primarily acts as an inhibitor for the activation of the proenzyme plasminogen to the enzyme plasmin, but also acts, depending upon its concentration, to either inhibit or to enhance the action of plasmin. Thus, it has been disclosed that ϵ-amino caproic acid acts as an inhibitor in concentrations above 0.03 M, while said amino acid is disclosed to exhibit an enhancing effect at lower concentrations up to about 0.02 M, the plasmin at the same time being present in concentrations from about 0.047 to about 0.229 units per ml, reference being made to the above definition of the plasmin unit (in the literature reference referred to a plasmin concentration range of 0.49 to 2.4 units per ml is mentioned, each 10.5 of these plasmin units being equal to 1 of the plasmin units defined in the foregoing).

The addition of amino acid in accordance with the present invention has also proved to augment the solubility of the plasmin in the aqueous medium. While a neutral solution of plasmin in water becomes turbid due to a precipitation of plasmin when the plasmin concentration is 0.01 unit and more per milliliter, it is possible by the addition of an amino acid to produce clear neutral plasmin solutions having a plasmin concentration up to 25 units per milliliter.

By the tests having led to the present invention and in which use has been made of a long series of different amino acids it has been found that the chemical structure of the amino acids influences their stabilizing effect. Thus it has proved to be appropriate to use preferably aliphatic amino monocarboxylic acids. Further it has been found appropriate that at least one amino group in the amino acid is bound to a carbon atom which by at least one carbon atom is separated from the carboxylic group(s) of the amino acid. Particularly appropriate are aliphatic amino monocarboxylic acids with more than 3 carbon atoms and a terminal amino group since the stabilizing effect obtainable seems to be the better the longer the distance is between the carboxylic group of the amino acid and its amino group(s).

Figure 2:
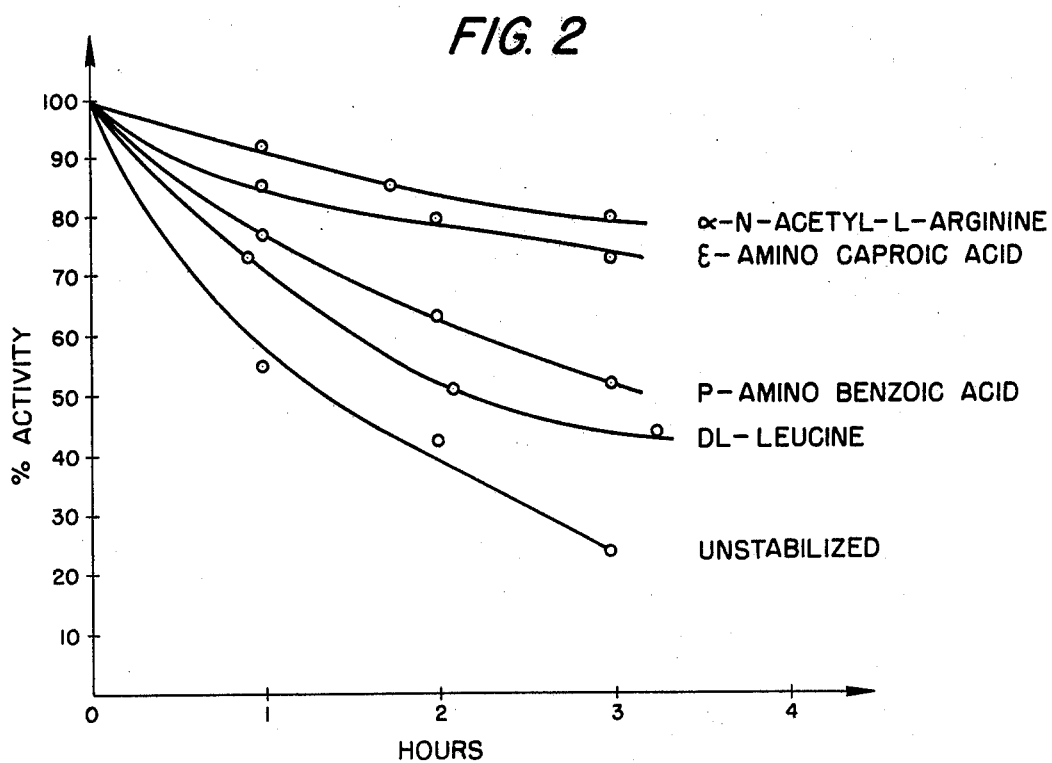

In order to illustrate the stabilizing effect obtainable according to the invention reference is made in the following to a series of stabilizing experiments, i.e. with regard to the drawing in which FIGS. 1 and 2 show graphically the stabilizing effect of different amino acids.

The stabilizing effect of a long series of amino acids has been examined in connection with plasmin originating from swine blood and dissolved in phosphate buffer (pH 7.5). An aqueous solution of the amino acid in question is mixed with the plasmin solution while diluting, if desired, in such proportions that the produced mixture contains about 0.4 plasmin unit per milliliter and 0.25 millimole of amino acid per plasmin unit if the solubility of the amino acids allows the said amino acid concentration. If not, a saturated amino acid solution is employed. The amino acid-containing plasmin solution thus produced is placed in a thermostat at 35.5°C, and at different hours samples are taken which are analysed for plasmin activity reckoned in per cent of the initial activity (about 0.4 unit per milliliter).

The results of the tests are compiled in the table below.

Table I

| Amino acid | % activity after 60 minutes at 35.5°C | % activity after 120 minutes at 35.5°C |
| --- | --- | --- |
| None | 55 | 43 |
| Glycine | 57 | 44 |
| Guanidino acetic acid | 80 | 68 |
| Creatine | 81 | 60 |
| β-analine | 72 | 66 |
| DL-valine | 60 | 49 |
| DL-leucine | 72 | 53 |
| DL-isoleucine | 77 | 57 |
| DL-norleucine | 72 | 59 |
| L(+)-aspartic acid | 60 | 51 |
| DL-methionine | 69 | 62 |
| γ-amino butyric acid | 97 | 87 |
| L(+)-citrulline | 64 | 54 |

Table I-continued

| Amino acid | % activity after 60 minutes at 35.5°C | % activity after 120 minutes at 35.5°C |
| --- | --- | --- |
| L-arginine | 78 | 65 |
| α-N-acetyl-L-arginine | 92 | 87 |
| L-ornithine | 92 | 81 |
| ε-amino caproic acid | 85 | 80 |
| L-lysine | 98 | 96 |
| m-amino benzoic acid | 73 | 52 |
| o-amino benzoic acid | 79 | 68 |
| p-amino benzoic acid | 77 | 63 |
| DL-phenyl analine | 73 | 55 |
| L-histidine | 64 | 61 |
| DL-thrypthophane | 60 | 48 |
| L(−)-proline | 62 | 54 |
| L(−)-hydroxyproline | 69 | 66 |
| Glycyl glycine | 88 | 77 |
| None | 55 | 43 |

The curves in FIGS. 1 and 2 show the stability obtainable under the above mentioned experimental conditions, also after storage at 35.5°C for a longer period of time, while using the mentioned amino acids, the abscissa of the curves indicating the storage period in hours and the ordinate the per cent of the original activity. For comparison the curve of stability of the employed plasmin solution without addition of amino acid is also shown.

It will appear from the experimental material that the stabilizing effect of aliphatic α-amino acids is not very big at the employed amino acid concentration, the stabilizing effect, however, increasing the longer the carbon chain of the α-amino acid is. If the carbon chain of the α-amino acid is branched, the stabilizing effect of the α-amino acid will also increase. Further, it will be seen that the stabilizing effect of α-amino acids will increase violently if the amino group is substituted to give the acid a more basic character. Thus, guanidino acetic acid and creatine show a stabilizing effect being considerably better than that of glycine and DL-valine. Moreover, it will be seen that an introduction of acid groups in an α-amino acid causes the stabilizing effect to decrease. Thus, the stabilizing effect of L(−)-aspargic acid is almost identical with that of glycine.

Aliphatic β-amino acids have a greater stabilizing effect than have α-amino acids, and with increasing distance between the carboxylic group of the amino acid and its amino group the stabilizing effect will increase. Thus, e.g. γ-amino butyric acids and ε-amino caproic acid stabilize considerably better than β-alanine.

The stabilizing effect will remain practically unchanged even if an amino group in α-position is present in addition to the amino group spaced considerably from the carboxylic group, compare the stabilizing effect of ε-amino caproic acid and lysine (α,ε-diamino caproic acid). Also ornithine (α,δ-diamino valeric acid) provides an excellent stabilizing effect.

Also with sulphurous amino acids it is possible to obtain a stabilizing effect, vide e.g. DL-methionine.

The fact that an amino group is substituted with a non-basic group does not prevent the occurrence of the stabilizing effect if the amino acid still has a basic group far away from the carboxylic group. Thus α-N-acetyl-L-arginine provides an excellent stabilizing effect.

While glycine only shows a faintly stabilizing effect in the employed concentration, a strongly stabilizing effect is obtained with glycyl glycine, which is in conformity with what has been mentioned above i.e. that it is important for the stabilizing effect that an amino group is present so far as possible from the carboxylic group of the amino acid.

The aromatic amino acids tested show a limited stabilizing effect in the employed concentrations. Something similar applies to the tested heterocyclic amino acids L(−)-proline and L(−)-hydroxy proline.

Glycyl glycine is to be considered a dipeptide. Also other dipeptides, e.g. leucyl glycine, alanyl alanine and glycyl valine and higher peptides, may be used though usually the ordinary amino acids are preferred due to the fact that they are more easily available and obtainable at a lower price.

Tests corresponding to the above mentioned ones in which use has been made of plasmin originating from swine blood, have also been carried out under the employment of plasmin originating from ox blood. In the table below the results obtained under the employment of the mentioned amino acids have been compiled.

Table II

| Amino acid 0.25 millimole per plasmin unit | % activity after 60 min. at 35.5°C | % activity after 120 min. at 35.5°C |
|---|---|---|
| L-lysine | 85 | 83 |
| L-arginine | 86 | 85 |
| ε-amino caproic acid | 100 | 99 |
| None | 60 | 45 |

It will appear from the table below that amino acids also have a stabilizing effect on solutions of plasmin originating from human blood. The experimental circumstances are identical to those mentioned above.

Table III

| Amino acid 0.25 millimole per plasmin unit | % activity after 60 min. at 35.5°C | % activity after 120 min. at 35.5°C |
|---|---|---|
| L-lysine | 87 | 78 |
| ε-amino caproic acid | 94 | 96 |
| None | 55 | 32 |

As it will appear from table I the stabilizing effect of glycine at a storage temperature of the plasmin solution of 35.5°C is rather insignificant when the glycine is used in an amount of 0.25 millimole per plasmin unit. It is, however, a general rule that an increase of the amino acid concentration within certain limits will cause an increased stability of the plasmin solutions. Thus, if use is made of an addition of glycine in a concentration of 2.5 millimole per plasmin unit, the plasmin solution will after storage at 35.5°C for 60 minutes show 73 per cent of its original activity compared with 57 per cent, only, of the original activity when the glycine has been added in a concentration of 0.25 millimole per plasmin unit. Something similar applies to the other amino acids which according to table I show a relatively insignificant stabilizing effect at the employed concentration.

If a relatively large amount of the amino acids as e.g. L-lysine or ε-amino caproic acids showing a strongly stabilizing effect is added to the plasmin solutions, and the solutions are analysed for plasmin activity immediately after the addition, a plasmin activity smaller than that expected will be found. This is probably due to the fact that the relatively high amino acid concentration will cause formation in appreciable amounts of a plasmin amino acid complex which is not active. If, however, the solutions are diluted before the analysis, the total plasmin activity will be found again. By way of illustration reference may be made to the following experiments:

a. A plasmin solution from swine blood and containing about 0.4 plasmin unit per milliliter and 2 millimoles of L-lysine per plasmin unit is produced in phosphate buffer (pH 7.5) whereafter the plasmin activity of the mixture is determined and compared with the activity of the plasmin solution without the amino acid addition and the activity of the mixture is expressed in per cent of the activity of the unmixed plasmin solution. Thereafter a dilution of the solution is carried out expressed in the original volume of the plasmin solution divided by the volume of the plasmin solution after the dilution, and the activity of the diluted solutions is determined. The results of these experiments are compiled in the table below.

Table IV

| Dilution | Millimole L-lysine per ml | Activity expressed in per cent of the total activity |
|---|---|---|
| Undiluted | 0.8 | 88 |
| 4:5 | 0.64 | 84 |
| 3:5 | 0.48 | 92 |
| 2:5 | 0.32 | 100 |
| 1:5 | 0.16 | 97 | b. The same experiment as mentioned sub a) is carried out except that use is made of ε-amino caproic acid instead of L-lysine. The results are compiled in the table below:

Table V

| Dilution | Millimole ε-amino caproic acid per ml | Activity expressed in per cent of the total activity |
|---|---|---|
| Undiluted | 0.8 | 57 |
| 4:5 | 0.64 | 65 |
| 3:5 | 0.48 | 71 |
| 2:5 | 0.32 | 84 |
| 1:5 | 0.16 | 93 |

As to the amount of amino acid which should be used in obtaining a stabilization utilizable in practice, it should first be mentioned that the stability both of a plasmin solution with no amino addition as well as of a plasmin solution with an addition of amino acid is highly dependent on the temperature at which the solution is stored. At 25°C the half-life period of an unstabilized plasmin solution is about 4 to 5 times bigger than at 35.5°C, provided use has been made of the same plasmin concentration. Also the stability of a plasmin solution which has been stabilized by an amino acid addition is very dependent on the temperature. In order to illustrate this reference may be made to the tables below which, just like table I, show the activity of a plasmin solution containing 0.4 and 0.3 plasmin units per ml, respectively, having varying amounts of L-lysine added thereto and having been stored for 60 minutes and 120 minutes, respectively, at 35.5°C and 25°C, respectively.

Table VI

| Millimole L-lysine per plasmin unit | % activity after 60 min. at 35.5°C | % activity after 120 min. at 35.5°C |
|---|---|---|
| 0.000 | 55 | 43 |
| 0.031 | 74 | 52 |
| 0.062 | 89 | 73 |
| 0.125 | 99 | 84 |

Table VI-continued

| Millimole L-lysine per plasmin unit | % activity after 60 min. at 35.5°C | % activity after 120 min. at 35.5°C |
| --- | --- | --- |
| 0.25 | 100 | 92 |

Table VII

| Millimole L-lysine per plasmin unit | % activity after 60 min. at 25°C | % activity after 120 min. at 25°C |
| --- | --- | --- |
| 0.00 | 77 | 70 |
| 0.005 | 88 | 78 |
| 0.010 | 91 | 84 |
| 0.021 | 99 | 91 |
| 0.042 | 100 | 99 |

If only a plasmin loss of about 20 per cent by standing for 2 hours at 25°C and 35.5°C, respectively, is to be allowed, it will be sufficient at the first mentioned temperature to have a lysine concentration of about 0.005 millimole per plasmin unit, while at 35.5°C a lysine concentration of about 0.1 millimole per plasmin unit will be necessary.

Thus it will be seen that the lower limit for the amino acid concentration utilizable in practice does not only depend on the kind of amino acid to be used, but also on the demands which in each individual case will be made on the part of the clinics so far as the stability of the employed plasmin solutions is concerned.

With lysine as an example it will be seen that in order to avoid a plasmin loss by standing for two hours at 35.5°C and a plasmin concentration of 0.4 mole per ml it will be necessary to employ a lysine concentration of above 0.25 millimole per plasmin unit while the corresponding lysine concentration at 25°C is 0.04 millimole per plasmin unit. In practice it will, however, not be necessary to make such heavy demands on the stability. It will be possible to tolerate an activity loss of 20 per cent during 2 hours at 25°C.

As to lysine, the lower limit of the amount of lysine necessary in practice may be fixed at 0.002 millimole per plasmin unit, and as lysine must be considered one of the amino acids having the most vigorous stabilizing effect use should always be made of at least 0.002 millimole of amino acid per plasmin unit in order to obtain a useful stabilizing effect. It is preferred that the amount of amino acid exceeds 0.005 millimole per plasmin unit, and it is usually appropriate to employ amino acid concentrations from about 0.02 to about 2.5 millimoles per plasmin unit, preferably from about 0.02 to about 1 millimole per plasmin unit, especially about 0.04 millimoles per plasmin unit.

As it will appear from table IV lysine will, when use is made of a plasmin concentration corresponding to ½ unit per millimole lysine, have an inactivating effect on the plasmin solution provided the lysine is present in a concentration above 0.32 millimole per ml. As, however, the inactivation, as it also appears from table IV, is reversible, since it disappears by dilution, and as the injection of the plasmin solutions, specially by infusion, causes a vigorous dilution of the plasmin solution to take place, and the removal of amino acids from blood and tissue fluids occurs many times more quickly than the removal of plasmin, it is for the purpose of the invention possible to use lysine in concentrations greatly exceeding 2 millimole per plasmin unit. Actually, there exists no physiological upper limit for the employed amino acid amount beyond the dosis having toxic effect and being of a magnitude quite different from the amino acid amounts necessary for the purpose of the invention.

For clinical reasons one will certainly for intravenous purposes in general hesitate to make use of a plasmin solution containing such an amount of amino acid that a part thereof is present in suspension in undissolved state in the plasmin solution. From a practical point of view the solubility of the amino acid is consequently to be considered as a guide for the maximal amino acid amount which should be used for intravenous injection, including infusion. The solubility of the different amino acids appears from the literature and is in most cases so big as to allow the stabilization aimed at, without the necessity of employing concentrated amino acid solutions.

If the plasmin solution is intended for infusion, the optimal amino acid concentration is the concentration giving the desired stability at the temperature of infusion (10° to 36°C) in the infusion period (up to 3–4 hours). Numerically it will be appropriate to use an amino acid concentration of 0.005 to 1 millimole per plasmin unit dependent on the employed amino acid.

In the tests referred to above use has been made of plasmin solutions having a plasmin content of 0.3 and 0.4 units, respectively, per milliliter. When using more concentrated solutions, e.g. containing 10 plasmin units per milliliter, an appreciable initial loss of plasmin will occur immediately by the adjustment of the pH-value from 2–3 up to neutral reaction unless amino acids are present in sufficient amounts. Thus, in the course of a few minutes an initial loss of 20 per cent may e.g. arise when an acidified plasmin solution containing 10 plasmin units per milliliter is adjusted to pH 7.5 at 25°C even if lysine is present in the solution in an amount of 0.002 millimole per plasmin unit. Such initial loss can, however, be avoided by increasing the amino acid concentration. With a lysine content of 0.04 millimole per plasmin unit it is possible under the above mentioned experimental conditions to avoid completely an initial loss.

In the production of concentrated plasmin solutions having neutral reaction the said circumstances should be taken into account.

In order to be suitable for clinical purposes the therapeutically useful plasmin compositions of the present invention should contain considerably more plasmin than 0.1 units per milliliter. Thus, in general plasmin compositions containing less than about 0.4 units per milliliter are considered unsuitable for use in the human clinic, since such low-concentrated solutions will have to be administered, e.g. by intravenous injection or infusion, preferably the latter, in such large volumes that the fluid balance of the human body will be seriously affected. In clinical practice, amino-acid stabilized plasmin solutions of the type disclosed in the foregoing will usually contain at least about 0.4 to 0.5 plasmin units per milliliter, preferably from about 2 to about 5 units per milliliter or more. Thus, it is also possible to employ for certain clinical purposes plasmin solutions containing considerably higher concentrations of plasmin, i.e. 5–20 units per milliliter, preferably 10–20 units per milliliter. Concentrations of about 25 units per milliliter and even more, may also be employed.

In order to obtain the desired stabilization according to the invention it is possible to proceed in different ways.

Thus, a plasmin solution may be produced which solution is sterile filtered whereafter the plasmin is isolated from the solution e.g. by freeze-drying, salting out or precipitation and is filled into vials if such filling has not already taken place during the isolating step. There is also produced an amino acid solution which is sterile filtered and is filled into vials. Immediately before use of the plasmin the plasmin from the vial is dissolved in the amino acid solution, thereby producing a sterile and stable plasmin solution ready for use.

It is also possible to produce a sterile filtered plasmin solution containing one or more amino acids and to bring the mixture into dry state, e.g. by freeze-drying or precipitation and to fill the dry mixture into vials. Immediately before use of the plasmin the dry mixture is dissolved in sterile water, a buffer solution or the like, whereby a stabilized plasmin preparation will be produced.

Further, it is possible to produce a sterile plasmin solution which is adjusted to pH 1 to 4. Such acid solution is stable for several months if it is stored at 4°–5°C. By mixing such solution before use with a sterile amino acid solution which has either been buffered with one of the normal acid-base-buffer systems or has a sufficient amino acid content, it is possible to obtain a neutral stable plasmin solution.

Finally, it is possible to produce a sterile plasmin solution containing the necessary amount of amino acid and having been adjusted to a pH-value of 1–5, preferably 2–3. By mixing such solution with a sterile aqueous solution which has either been buffered with one of the normal acid-base-buffer systems, or which merely contains sufficient base, it is possible to arrive at a neutral and stable plasmin solution.

In order to further illustrate the practical realization of the invention reference is made to the below examples 1 to 6 showing the production of stabilized plasmin solutions, preferably useful for infusion purposes.

Example 1

50 ml of a plasmin solution having a pH-value of 2.5 and containing 10 plasmin units per ml are sterile filtered, freeze-dried and filled into vials. 50 ml of 0.2 molar phosphate buffer containing lysine in a concentration of 0.4 mole per liter are sterile filtered and filled into vials, too. Immediately before the use of the plasmin the freeze-dried plasmin is dissolved in the lysine solution whereby a sterile stabilized plasmin preparation having pH 7.5 is obtained.

Example 2

50 ml of a plasmin solution having a pH-value of 7.5 and containing 10 plasmin units per ml and 0.1 mole ε-amino caproic acid per liter are sterile filtered, freeze-dried and filled into vials. Immediately before the use of the plasmin the freeze-dried preparation is dissolved in 50 ml of distilled water whereby a sterile stabilized plasmin preparation having pH 7.5 is obtained.

EXAMPLE 3

45 ml of a plasmin solution having a pH-value of 2.5 and containing 20 plasmin units per ml are sterile filtered and filled into vials. 10 ml of 1 molar phosphate buffer (pH 7.5) containing lysine in a concentration of 1 mole per liter, are sterile filtered and filled into vials, too. Immediately before the use of the plasmin solution 5 ml of the lysine solution are added thereto, whereby a sterile stabilized plasmin preparation having a pH-value of 7.5 is produced.

EXAMPLE 4

45 ml of a plasmin solution having a pH-value of 3.0 and containing 6 plasmin units per ml and 948 mg of L-arginine hydrochloride are sterile filtered and filled into vials. 10 ml of 1 molar phosphate buffer are sterile filtered and filled into vials, too. Immediately before the use of the plasmin solution 5 ml of the phosphate buffer are added thereto, whereby a sterile stabilized plasmin preparation with pH 7.0 is arrived at.

EXAMPLE 5

A solution of plasmin in diluted sulphuric acid having pH 2—3 is sterile filtered and freeze-dried. A solution of L-lysinemonohydrochloride in phosphate buffer is sterile filtered and freeze-dried. The freeze-dried substances are mixed together in such proportions that the mixture contains 0.04 millimole of lysine per plasmin unit. An amount of the produced mixture corresponding to 500 plasmin units is under sterile conditions transferred to an infusion bottle having a volume of 500 ml, and the bottle is sealed after partial evacuation. Immediately before the use an injectable solvent in appropriate amount is added to the bottle, e.g. in the form of sterile distilled water, a sterile glucose solution or sterile salt water. The said addition is facilitated due to the partial vacuum in the bottle. The pH-value of the solution will be between 7.0 and 7.5.

EXAMPLE 6

To 1 liter of a plasmin solution having pH 2.5 and containing 5.0 units of plasmin per milliliter 36.6 g of L-lysine monohydrochloride are added at 0° to 5°C. When the lysine has been dissolved pH is adjusted to 7.5 and still at 0° to 5°C 1.02 g of $KH_2PO_4$ and 7.56 g of $Na_2HPO_4, 2H_2O$ are added. After the phosphate buffer is dissolved the solution is sterile filtered.

The sterile filtered solution is filled into infusion bottles and is freeze-dried. 50 ml of plasmin solution per infusion bottle (300 ml) are used. After freeze-drying the bottles are sealed and labelled.

If desired the sterile filtered solution may be freeze-dried as a whole and the produced powder may thereafter be ground and filled into the infusion bottles.

The effect of the stabilized plasmin solutions according to the invention which solutions have been produced from swine blood, has been tested with excellent results both in experiments with animals and in the clinics. The clinical experiments did not show any antigen effect by the use of the plasmin. Due to the stabilization the employed plasmin solutions contain less amounts of plasmin being decomposed by autolysis giving rise to toxic secondary effects.

In the above examples solutions containing from 1 to 18 plasmin units per ml are obtained. There is, however, nothing to prevent from producing more or less concentrated solutions, e.g. down to 0.02 plasmin units and up to 25 plasmin units per ml or more.

The following examples demonstrate the clinical utility of lysine stabilized plasmin compositions of the invention in connection with their use in intravenous infusion in the human therapy of severe thromboembolic conditions, especially thrombophlebitis and pulmonary embolism. Initial plasmin infusion doses of from about 2 to about 15 plasmin units per kg body weight were given, and in many cases the preferred initial dose will vary from about 10 to about 20 plasmin units per kg body weight.

EXAMPLE A

A number of patients with venous Thrombophlebitis were treated with lysine stabilized plasmin by way of intravenous infusion. A lysine concentration of 0.04 millimoles per plasmin unit was employed, and initial doses as mentioned above were given. Usually an intravenous infusion of one hour's duration was given, followed in some cases by maintenance doses slowly infused during several hours. To counteract the hypercoagulability 10 units of heparin were given per 1 unit of plasmin.

All but one patient improved a few hours after or even during the intravenous infusion. Tenderness and pain disappeared, and the patients were able to walk. However, the oedema was practically unchanged 24 hours after the treatment, but venous stases subsided, and the Homann's sign was negative shortly after the therapy. The only complication seen was a rise in temperature and occasional chills during or just after the intravenous infusion. These were easily counteracted by the use of antipyretics.

The results obtained are summarized in the following table:

Table VIII

| Sex | Patient Age | Duration of Symptoms | Total dose of Plasmin infused | Reaction | Results |
|---|---|---|---|---|---|
| male | 22 years | 10–14 days | 1000 units | fever | 1–2 hr. no pain 1 day minimal edema |
| male | 31 years | 7 days | 1000 units 500 units 1000 units | fever | improved 1 day, slight edema, pain gone |
| male | 36 years | 2 days | 1000 units | none | no symptoms 1 day |
| female | 46 years | 6 hours | 1200 units | fever | no symptoms 1 day |
| male | 46 years | 1 day | 500 units | fever | improved 2 hr. + edema |
| male | 54 years | 5–6 days | 500 units 500 units | none | no symptoms after 1 hr. |
| male | 60 years | 2 days | 750 units 600 units 500 units | fever chills | pain gone, edemata disappeared gradually |
| female | 61 years | 6–7 days | 1500 units | fever | no symptoms after 1 hr. |
| male | 62 years | 4 days | 500 units | chills | improved 1 day |
| female | 78 years | 10–12 days | 1250 units | fever | pain gone, no edema after 3–4 days |

EXAMPLE B

A few patients who suffered from severe Pulmonary embolism were treated by way of plasmin therapy in a manner corresponding to the one described above. The clinical results were as follows:

Table IX

| Sex | Patient Age | Duration of Symptoms | Total dose of Plasmin used | Reaction | Results |
|---|---|---|---|---|---|
| female | 67 years | 3–4 days | 420 units | fever chills | complete relief of the symptoms |
| male | 80 years | 2 hours | 500 units | none | symptoms disappeared in 3 hr. |

What I claim and desire to be secured by letters Patent is:

1. A method for the clinical use of therapeutically useful compositions suitable for plasmin therapy of animals and humans, which comprises administering parenterally a composition consisting essentially of plasmin in an amount of about 2 to about 25 plasmin units per milliliter as the essential active ingredient together with about 0.04 to about 2.5 millimoles of a non-toxic amino acid per plasmin unit, said non-toxic amino acid being selected from aliphatic amino acids containing from 2 to 6 carbon atoms, amino benzoic acid, histidine, tryptophane, phenylalanine, proline and hydroxy proline.

2. In a method for the preparation of a therapeutically useful composition consisting essentially of plasmin, the improvement which comprises stabilizing the therapeutic activity of plasmin in a solution thereof at a pH of about 7 by including in a solution consisting essentially of plasmin in an amount of 0.4 to 25 plasmin units per ml. at least one amino acid selected from aliphatic amino acids containing from 2 to 6 carbon atoms, amino benzoic acid, histidine, tryptophane, phenylalanine, proline and hydroxy proline, in an amount of 0.25 to 2.5 millimoles per plasmin unit, the stability of said plasmin increasing with an increasing amount of said amino acid.

3. A therapeutically useful stabilized composition consisting essentially of plasmin in an amount of from 0.4 to about 25 plasmin units per milliliter as the essential active ingredient together with from 0.002 to 2.5 millimoles of at least one non-toxic amino acid per plasmin unit, stabilizing said plasmin to retain therapeutic plasmin activity thereof in solution at a pH of about 7, the minimum quantity of said amino acid varying from 0.002 to 0.25 millimole per plasmin unit in dependence upon the selected amino acid, said amino acid being selected from aliphatic amino acids containing from 2 to 6 carbon atoms, amino benzoic acid, histidine, tryptophane, phenylalanine, proline and hydroxy proline.

4. A therapeutically useful composition as defined in claim 3 wherein said amino acid has at least one amino group bound to a carbon atom which is spaced by at least one carbon atom from all carboxylic groups of said amino acid.

5. A therapeutically useful composition as defined in claim 3 wherein said amino acid has at least one amino group bound to a carbon atom which is spaced by at least one carbon atom from all carboxylic groups of said amino acid and wherein said amino acid is present in an amount of about 0.25 to about 2.5 millimoles per plasmin unit.

6. A therapeutically useful composition as defined in claim 18 wherein said amino acid is an aliphatic amino monocarboxylic acid.

7. A method for the clinical use of therapeutically useful compositions suitable for plasmin therapy of animals and humans, which comprises administering parenterally a composition consisting essentially of plasmin in an amount of from 0.4 to about 25 plasmin units per milliliter as the essential active ingredient together with from 0.002 to 2.5 millimoles of at least one non-toxic amino acid per plasmin unit stabilizing said plasmin to retain therapeutic plasmin activity thereof in solution at a pH of about 7, the minimum quantity of said amino acid varying from 0.02 to 0.25 millimole per plasmin unit in dependence upon the selected amino acid, said amino acid being selected from the group consisting of glycine, guanidino acetic acid, creatine, β-analine, valine, leucine, isoleucine, norleucine, aspartic acid, methionine, γ-amino butyric acid, citrulline, arginine, α-N-acetylarginine, ornithine, ϵ-amino caproic acid, lysine, m-amino benzoic acid, o-amino benzoic acid, p-amino benzoic acid, phenyl alanine, histidine, tryptophane, proline, hydroxyproline and glycyl glycine.

8. A method for the clinical use of therapeutically useful compositions suitable for plasmin therapy as defined in claim 7 wherein said composition contains plasmin in an amount of from 1 to 20 plasmin units per milliliter as the essential active ingredient together with 0.02 to 2.5 millimoles of said non-toxic amino acid per plasmin unit and wherein said composition is administered by way of intravenous infusion.

9. A method for the clinical use of therapeutically useful compositions suitable for plasmin therapy as defined in claim 7 wherein said composition contains plasmin in an amount of from 1 to 20 plasmin units per milliliter as the essential active ingredient together with 0.02 to 2.5 millimoles of said non-toxic amino acid per plasmin unit and wherein said composition is administered by way of intravenous injection.

10. A method for the clinical use of therapeutically useful compositions suitable for plasmin therapy as defined in claim 7 wherein said composition contains plasmin in an amount of from 2 to 20 plasmin units per milliliter as the essential active ingredient together with 0.02 to 2.5 millimoles per plasmin unit of said amino acid, said amino acid being selected from the group consisting of ϵ-aminocaproic acid and α,γ-diaminocaproic acid and wherein said composition is administered by way of intravenous infusion.

11. A therapeutically useful stabilized composition consisting essentially of plasmin in an amount of from 0.4 to about 25 plasmin units per milliliter as the essential active ingredient together with from 0.002 to 2.5 millimoles of at least one nontoxic amino acid per plasmin unit, stabilizing said plasmin to retain therapeutic plasmin activity thereof in solution at a pH of about 7, the minimum quantity of said amino acid varying from 0.002 to 0.25 millimole per plasmin unit in dependence upon the selected amino acid, said amino acid being selected from the group consisting of glycine, guanidino acetic acid, creatine, β-analine, valine, leucine, isoleucine, norleucine, aspartic acid, methionine, γ-amino butyric acid, citrulline, arginine, α-N-acetylarginine, ornithine, ϵ-amino caproic acid, lysine, m-amino benzoic acid, o-amino benzoic acid, p-amino benzoic acid, phenyl alanine, histidine, tryptophane, proline, hydroxyproline and glycyl glycine.

12. A therapeutically useful stabilized composition as defined in claim 11 containing plasmin as the essential active ingredient in an amount of from 0.4 to about 25 plasmin units per milliliter together with about 0.25 to about 2.5 millimoles of at least one of said amino acids per plasmin unit.

13. A therapeutically useful stabilized composition as defined in claim 11 containing about 2 to about 20 units of plasmin per milliliter as the essential active ingredient together with about 0.04 to about 2.5 millimoles of at least one of said amino acids per plasmin unit, stabilizing said plasmin while retaining therapeutic plasmin activity thereof in solution, at a pH of about 7, the minimum quantity of said amino acid varying from 0.04 to 0.25 millimole per plasmin unit in dependence upon the selected amino acid.

14. A therapeutically useful stabilized composition as defined in claim 11 containing about 5 to 20 units of plasmin per milliliter as the essential active ingredient together with 0.02 to 1 millimole of at least one of said amino acids per plasmin unit, stabilizing said plasmin while retaining therapeutic plasmin activity thereof in solution at a pH of about 7, the minimum quantity of said amino acid varying from 0.02 to 0.25 millimole per plasmin unit in dependence upon the selected amino acid.

15. A therapeutically useful composition as defined in claim 11, in which said amino acid is selected from the group consisting of ϵ-aminocaproic acid and lysine.

16. A therapeutically useful composition as defined in claim 11 wherein said plasmin as said essential active ingredient is present in an amount of from 1 to about 20 plasmin units per milliliter together with 0.02 to 2.5 millimoles of said non-toxic amino acid per plasmin unit.

17. A therapeutically useful composition as defined in claim 16, wherein said amino acid is selected from the group consisting of ϵ-aminocaproic acid and α,γ-diaminocaproic acid.

18. A therapeutically useful composition as defined in claim 17 in which said amino acid is present in an amount of about 0.04 millimoles per plasmin unit.

* * * * *